US00PP09695P

United States Patent [19]

Zaiger et al.

[11] Patent Number: Plant 9,695

[45] Date of Patent: Nov. 19, 1996

[54] PEACH TREE "SWEET SCARLET"

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 541,292

[22] Filed: Oct. 10, 1995

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

Our new development is a distinct variety of peach tree which has the following unique combination of features that are outstanding in a new variety.

1. Fruit with good flavor and eating quality.
2. Vigorous upright in growth.
3. Heavy and regular production of fruit.
4. Fruit staying firm on the tree 10 to 12 days after maturity (shipping ripe).
5. Fruit with good handling and shipping quality.
6. Fruit with a high degree of attractive red skin color.

1 Drawing Sheet

ORIGIN OF THE VARIETY

The present new variety of peach tree was originated by us in our experimental orchard located near Modesto, calif., as a first generation cross between a seedling selection with the field indentification number 39EB706 and Sweet Gem Peach (U.S. Plant Pat. No. 7,952). The female parent 39EB706 originated from a cross between two selected seedlings, 32EA300 and 11E284. The seedling selection 32EA300 originated from a cross between O'Henry Peach (U.S. Plant Pat. No. 2,964) and Giant Babcock Peach (U.S. Plant Pat. No. 1,353). The seedling selection 11E284 originated from seed of an open pollinated Red Grand Nectarine (U.S. Plant Pat. No. 1,060). A large group of these first generation seedlings were grown and maintained under close observation, during which time we recognized the desirable fruit characteristics of the present new variety and selected it for asexual reproduction and commercialization.

ASEXUAL REPRODUCTION OF THE VARIETY

The new and distinct variety of peach tree was asexually reproduced by budding, as performed by us in our experimental orchard located near Modesto, Calif. which shows that such reproduction run true to the original tree and are established and transmitted through succeeding propagations.

SUMMARY OF THE VARIETY

The present new variety of peach tree is of large size, vigorous upright growth and is a regular and productive bearer of large, firm, yellow flesh, clingstone fruit with an attractive red skin color. The fruit is further characterized by having good flavor and eating quality, holding firm on the tree 10 to 12 days after maturity (shipping ripe) and having good handling and storage quality. In comparison to its pollen parent Sweet Gem Peach (U.S. Plant Pat. No. 7,952) the fruit of the new variety is approximately one week earlier in maturity.

DESCRIPTION OF THE PHOTOGRAPH

The accompanying color photograph show typical specimens of the fruit and foliage of our new variety of peach tree. The upper and lower surface of the leaves are illustrated as are fruit specimens showing the exterior and a sectional view of a fruit divided in the suture plane to show flesh coloration, pit cavity and a stone remaining in place. The photograph was taken shortly after the fruit was picked at maturity (firm ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of the specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearing.*—Regular.
- *Shape.*—Usually pruned to vase shape.

Trunk:
- *Size.*—Medium to large.
- *Surface.*—Medium shaggy.
- *Color.*—Brown to coffee brown (5-E-8) to (5-F-8).

Branches:
- *Size.*—Medium.
- *Surface.*—Smooth to medium rough — varies with age of growth.
- *Lenticels.*—Numerous. Medium in size.
- *Color.*—Light brown to brown. Varies with age of growth.

Leaves:
- *Size.*—Large. Average length 6½". Average width 1½".
- *Form.*—Lanceolate. Pointed.
- *Texture.*—Smooth.
- *Margin.*—Serrulate.
- *Petiole.*—Medium length. Medium thickness.
- *Glands.*—Reniform. Number varies from 2 to 3. Average number 2. Medium size. Located on upper portion of petiole and lower portion of leaf blade.
- *Color.*—Upper surface — green to dark green (28-F-5) to (28-F-6). Lower surface — green to dull green (28-E-6) to (28-E-7).

Flower buds:
- *Size.*—Large.

*Form.*—Plump.
*Pubescence.*—Pubescent.

Flowers:
*Size.*—Large — showy.
*Blooming period.*—Mar. 4, 1994 to Mar. 8, 1994. Varies slightly with weather conditions.
*Pollen.*—Present.
*Color.*—Pink.

Fruit:
*Maturity when described.*—Firm ripe.
*Date of first picking.*—Jun. 4, 1994.
*Date of last picking.*—Jun. 9, 1994.
*Size.*—Large. Average diameter axially 2⅞" to 3". Average transversely in suture plane 2⅞" to 3".
*Form.*—Nearly globose.
*Suture.*—Shallow — extends from base to apex.
*Ventral surface.*—Round — nearly smooth.
*Apex.*—Usually round, varies from slight pistil point to rounded.
*Base.*—Retuse.
*Cavity.*—Rounded to slightly elongated in suture plane. Average depth ½". Average width 1".

Flesh:
*Ripens.*—Evenly.
*Texture.*—Firm.
*Fibers.*—Moderate number, small, tender.
*Juice.*—Moderate.
*Aroma.*—Moderate.
*Flavor.*—Good, very mild, sub-acid, sweet.
*Eating quality.*—Good.
*Amygdalin.*—Undetected.
*Color.*—Maize yellow to sunflower yellow (4-A-6) to (4-A-7). Pit cavity — amber yellow to chinese yellow (4-B-6) to (4-B-7).

Skin:
*Thickness.*—Medium.
*Texture.*—Medium.
*Tendency to crack.*—None.
*Down.*—Moderate — short.
*Color.*—Yellow ground color (4-A-4) to (4-A-5). Overspread with red to lake red (9-C-7) to (9-C-8).

Stone:
*Size.*—Large. Average length 1⅜". Average breadth 1". Average thickness ½.
*Type.*—Clingstone.
*Form.*—Ovoid.
*Apex.*—Acute.
*Base.*—Usually rounded — varies from rounded to straight.
*Sides.*—Equal to unequal.
*Tendency to split.*—None.
*Surface.*—Irregular furrowed toward apex, pitted toward bsae. Pits vary from round to elongated.
*Ridges.*—Round.
*Color.*—Light brown to brown (5-D-6) to (6-D-6).

Use: Dessert.
*Market.*—Local and long distance.

Keeping quality: Good.
Shipping quality: Good.

The present variety of peach tree, its flowers, foliage and fruit, herein described may vary in slight detail due to climate, soil conditions and cultural practices under which the variety may be grown. The present description is that of the variety grown by us under the ecological conditions prevailing near Modesto, Calif.

We claim:

1. A new and distinct variety of peach tree, substantially as illustrated and described, characterized by its large size, vigorous upright growth, is a regular and productive bearer of large, yellow flesh, clingstone fruit with an attractive red skin color; the fruit is further characterized by having firm flesh with a sweet sub-acid flavor, having the ability to ship to long distance markets and in comparison to Sweet Gem Peach (U.S. Plant Pat. No. 7,952) the fruit is approximately 1 week early in maturity.

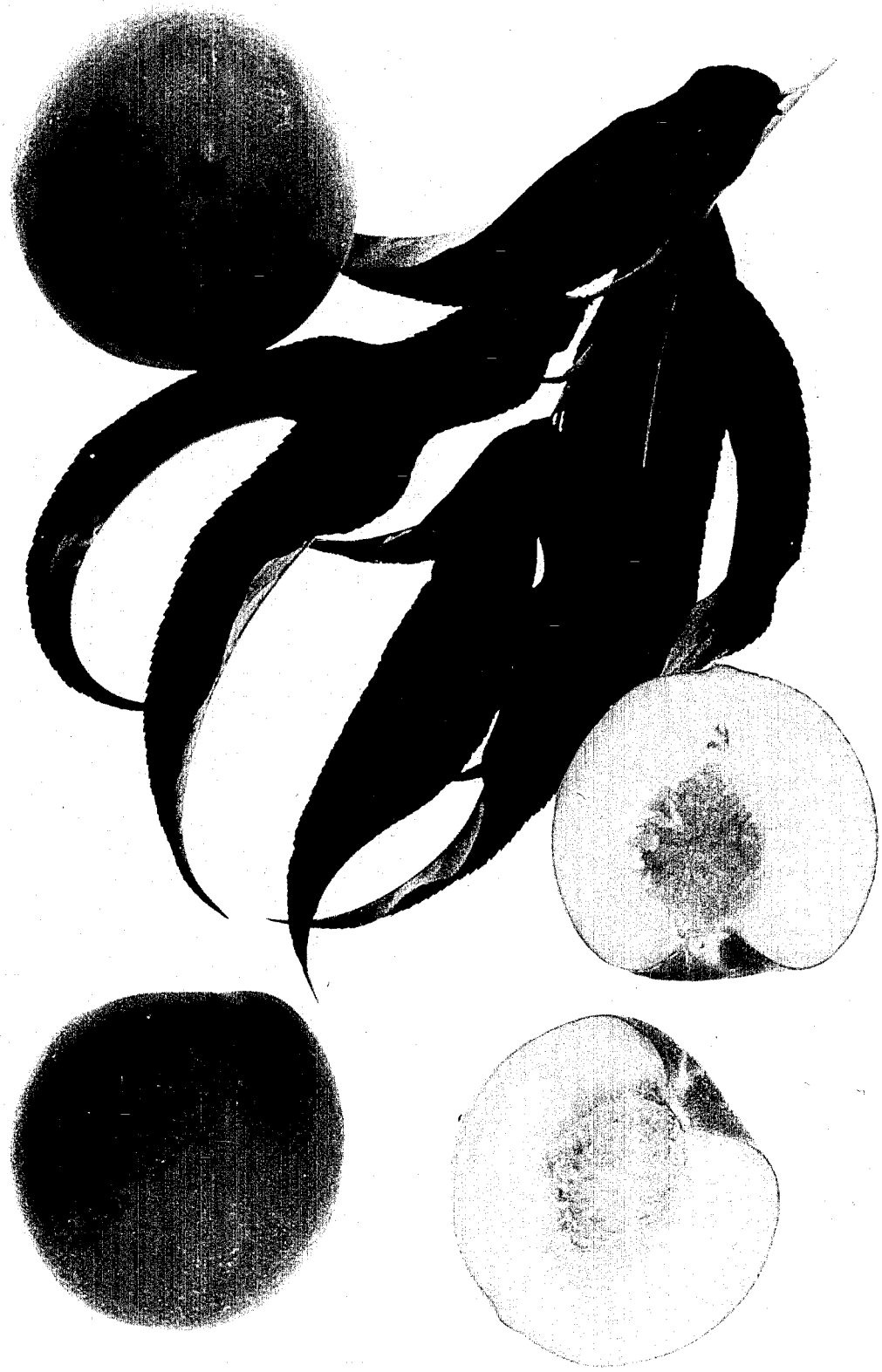

* * * * *